US009993571B2

(12) United States Patent
Lin et al.

(10) Patent No.: US 9,993,571 B2
(45) Date of Patent: Jun. 12, 2018

(54) MULTI-WAVELENGTH ULTRAVIOLET LIGHT SANITIZING SYSTEMS AND METHODS

(71) Applicant: THE BOEING COMPANY, Chicago, IL (US)

(72) Inventors: Chao-Hsin Lin, Redmond, WA (US); Roveyln T. Dytioco, Seattle, WA (US); Sharon L. Norris, Renton, WA (US)

(73) Assignee: The Boeing Company, Chicago, IL (US)

( * ) Notice: Subject to any disclaimer, the term of this patent is extended or adjusted under 35 U.S.C. 154(b) by 0 days. days.

(21) Appl. No.: 15/245,251

(22) Filed: Aug. 24, 2016

(65) Prior Publication Data

US 2018/0055959 A1    Mar. 1, 2018

(51) Int. Cl.
*A61L 2/10* (2006.01)
*B64D 11/02* (2006.01)

(52) U.S. Cl.
CPC ............... *A61L 2/10* (2013.01); *B64D 11/02* (2013.01); *A61L 2202/14* (2013.01); *A61L 2202/25* (2013.01); *A61L 2209/12* (2013.01); *A61L 2209/14* (2013.01)

(58) Field of Classification Search
CPC ........ A61L 2/00; A61L 2/0029; A61L 2/0047; A61L 9/00; A61L 9/18; A61L 9/20; A61L 12/00; A61L 12/02; A61L 12/06; A61L 12/063; A61L 2202/00; A61L 2202/122
USPC .............. 250/453.11, 454.11, 455.11, 504 R; 422/22, 24
See application file for complete search history.

(56) References Cited

U.S. PATENT DOCUMENTS

| 4,317,041 A | 2/1982 | Schenck |
| 4,819,276 A | 4/1989 | Stevens |
| 5,843,374 A | 12/1998 | Sizer et al. |
| 6,254,625 B1 | 7/2001 | Rosenthal |
| 8,168,963 B2 | 5/2012 | Ratcliffe |

(Continued)

FOREIGN PATENT DOCUMENTS

| EP | 2391421 A1 | 12/2011 |
| EP | 1866627 B1 | 9/2013 |
| WO | WO 2014036217 | 3/2014 |

OTHER PUBLICATIONS

"Kinetics of Microbial Inactivation for Alternative Food Processing Technologies Ultraviolet Light" U.S. Food and Drug Administration,,  http://www.fda.gov/Food/FoodScienceResearch/SafePracticesforFoodProcesses/ucm103137.htm.

(Continued)

*Primary Examiner* — Nicole Ippolito
(74) *Attorney, Agent, or Firm* — Joseph M. Butscher; The Small Patent Law Group, LLC (57) ABSTRACT

An ultraviolet (UV) light sanitizing system is configured to sanitize a structure. The UV light sanitizing system includes a UV light assembly that is configured to emit UV light onto the structure, and a UV light emission control unit coupled to the UV light assembly. The UV light emission control unit is configured to control the UV light assembly to emit UV light onto the structure within at least a first UV band and a second UV band that differs from the first UV narrow band during a sanitizing cycle that sanitizes the structure. The UV light within the first and second UV bands is configured to kill at least one type of microbe.

20 Claims, 6 Drawing Sheets

(56) References Cited

U.S. PATENT DOCUMENTS

| | | |
|---|---|---|
| 8,481,985 B2 | 7/2013 | Neister |
| 8,753,575 B2 | 6/2014 | Neister |
| 8,859,994 B2 | 10/2014 | Deal |
| 8,907,304 B2 | 12/2014 | Kreitenberg |
| 8,975,605 B2 | 3/2015 | Neister |
| 9,144,618 B2 | 9/2015 | Kreitenberg |
| 9,149,549 B2 | 10/2015 | Kreitenberg |
| 9,550,006 B2 | 1/2017 | Boodaghians et al. |
| 2005/0173652 A1 | 8/2005 | Ressler |
| 2008/0035864 A1* | 2/2008 | Fiset .............. A61N 5/0614 250/504 R |
| 2014/0017135 A1 | 1/2014 | Boodaghians et al. |
| 2014/0059796 A1 | 3/2014 | Boodaghians et al. |
| 2014/0115764 A1 | 5/2014 | Cheng |
| 2014/0140888 A1 | 5/2014 | Neister |
| 2014/0227132 A1 | 8/2014 | Neister |
| 2015/0062893 A1* | 3/2015 | Lynn .................. A61L 2/10 362/231 |
| 2016/0089459 A1 | 3/2016 | Boodaghians et al. |
| 2016/0220716 A1 | 8/2016 | Childress |

OTHER PUBLICATIONS

Brian Oram, "UV Disinfection Drinking Water", http://www.water-research.net/index.php/water-treatment/water-disinfection/uv-disinfection.

Nicholas G. Reeda, "The History of Ultraviolet Germicidal Irradiation for Air Disinfection"Public Health Reports / Jan.-Feb. 2010 / vol. 125, pp. 15-27.

SangWoo Kim, et al,"In Vitro Bactericidal Effects of 625, 525, and 425nm Wavelength (Red, Green, and Blue) Light-Emitting Diode Irradiation", Photomedicine and Laser Surgery, vol. 31, No. 11, 2013, Mary Ann Liebert, Inc., pp. 554-562.

Michelle Maclean, "Inactivation of Bacterial Pathogens following Exposure to Light from a 405-Nanometer Light-Emitting Diode Array", Applied and Environmental Microbiology, Apr. 2009, vol. 75, No. 7 p. 1932-1937.

Extended European Search Report for EP 17179864.8-1370, dated Dec. 21, 2017.

* cited by examiner

MULTI-WAVELENGTH ULTRAVIOLET LIGHT SANITIZING SYSTEMS AND METHODS

FIELD OF THE DISCLOSURE

Embodiments of the present disclosure generally relate to ultraviolet light sanitizing systems and methods, and, more particularly, to multi-wavelength ultraviolet light sanitizing systems and methods.

BACKGROUND OF THE DISCLOSURE

Commercial aircraft are used to transport passengers between various locations. A typical commercial aircraft includes one or more lavatories within an internal cabin.

Systems are currently being developed to disinfect or otherwise sanitize surfaces within aircraft lavatories that use ultraviolet (UV) light. For example, it has been found that far UV light efficiently disinfects exposed surfaces within a lavatory.

In order to sanitize a surface of a structure, a known UV light sterilization method emits a broad spectrum UVC light onto the structure. However, UVC light typically takes a significant amount of time (for example, three minutes) to kill various microbes. Further, various microbes may not be vulnerable to UVC light. That is, such microbes may be able to withstand exposure to UVC light.

Also, certain types of microbes may develop a resistance to UVC light. For example, while UVC light may initially kill certain types of microbes, with continued exposure to UVC light over time, the particular species of microbe may develop a resistance to UVC light and able to withstand UVC light exposure.

SUMMARY OF THE DISCLOSURE

A need exists for a system and method of efficiently and effectively sanitizing a structure using ultraviolet light. A need exists for a system and method to eradicate a wide variety of microbes from a structure.

With those needs in mind, certain embodiments of the present disclosure provide an ultraviolet (UV) light sanitizing system that is configured to sanitize a structure. The UV light sanitizing system includes a UV light assembly that is configured to emit UV light onto the structure, and a UV light emission control unit coupled to the UV light assembly. The UV light emission control unit is configured to control the UV light assembly to separately emit UV light onto the structure within at least a first UV band and a second UV band that differs from the first UV narrow band during a sanitizing cycle that sanitizes the structure. The UV light within the first and second UV bands is configured to kill at least one type of microbe.

In at least one embodiment, the first UV band includes one of a far UV light range, a UVC light range, a UVB light range, a UVA light range, or a vacuum UV light range within the UV spectrum. The second UV band includes another of the far UV light range, the UVC light range, the UVB light range, the UVA light range, or the vacuum UV light range.

The UV light emission control unit controls the UV light assembly to emit the UV light within the first UV band at a first time period and to emit the UV light within the second UV band at a second time period. The first time period may differ from the second time period. In at least one embodiment, the second period of time sequentially follows the first period of time. In at least one other embodiment, the first time period is concurrent with the second time period. In at least one embodiment, the first time period at least partially overlaps the second time period.

The UV light assembly may include a plurality of UV light elements. A first one of the plurality of UV light elements may be configured to emit the UV light within the first UV band, and a second one of the plurality of UV light elements may be configured to emit the UV light within the second UV band. Optionally, the UV emission control unit is configured to modulate the UV light emitted by the plurality of UV light elements to selectively emit the UV light within the first and second UV bands.

The UV light assembly may include at least one filter coupled to the plurality of UV light elements. The filter is configured to filter the UV light with respect to the first and second UV bands.

Certain embodiments of the present disclosure provide an ultraviolet (UV) light sanitizing method that is configured to sanitize a structure. The UV light sanitizing method includes coupling a UV light emission control to a UV light assembly, and emitting UV light from the UV light assembly onto the structure. The emitting includes using the UV light emission control unit to control the UV light assembly to separately emit the UV light onto the structure within at least a first UV band and a second UV band that differs from the first UV narrow band during a sanitizing cycle that sanitizes the structure. The UV light within the first and second UV bands is configured to kill at least one type of microbe.

Certain embodiments of the present disclosure provide a vehicle that includes an internal cabin, a lavatory within the internal cabin, and an ultraviolet (UV) light sanitizing system that is configured to sanitize at least one structure within the lavatory.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a programmable multi-wavelength ultraviolet (UV) light sanitizing system that is configured to selectively emit narrow bands of UV light across the UV spectrum. In at least one embodiment, the UV light sanitizing system is configured to emit UV light within two or more of a far UV light range, a UVC light range, a UVB light range, a UVA light range, and a vacuum UV light range. The types of UV light may be selected based on the types of microbes (for example, bacteria, germs, fungi, viruses, spores, and the like) that may be present on a particular structure. As such, the UV light sanitizing system may be specifically tailored to kill particular types of microbes with different types of UV light. The UV light sanitizing system emits multiple high energy, narrow bands of different types of UV light (in contrast to a single broad band of UV light) which more effectively and efficiently sanitizes a structure, such as a toilet, cabinet, sink, floor, or the like within a lavatory.

The UV light sanitizing system may be configured to vary the duration, frequency, order, and/or the like of emitted UV light to efficiently sanitize a structure, while consuming less power than a typical broad spectrum system. In at least one embodiment, the UV light sanitizing system includes a wide irradiance source and one or more filters that are configured to filter the emitted light with respect to desired UV wavelengths and frequencies. In at least one other embodiment, the UV light sanitizing system includes a plurality of UV light elements (for example, lasers, lamps, light emitting diodes, microfilaments, and/or the like), which are configured to emit UV light at different wavelengths and frequencies.

Certain embodiments of the present disclosure provide a sanitizing method that includes identifying an area to be sanitized, and sequentially exposing the area to at least two narrow bands of UV light. The exposure may last ten seconds or less for each narrow bands of UV light, which reduces power consumption. Each of the narrow bands of UV light includes at least one non-overlapping bandwidth of UV light. In at least one embodiment, the total exposure may be one minute or less. Each narrow band may be particularly suited to kill one or more particular microbes.

Figure 1:
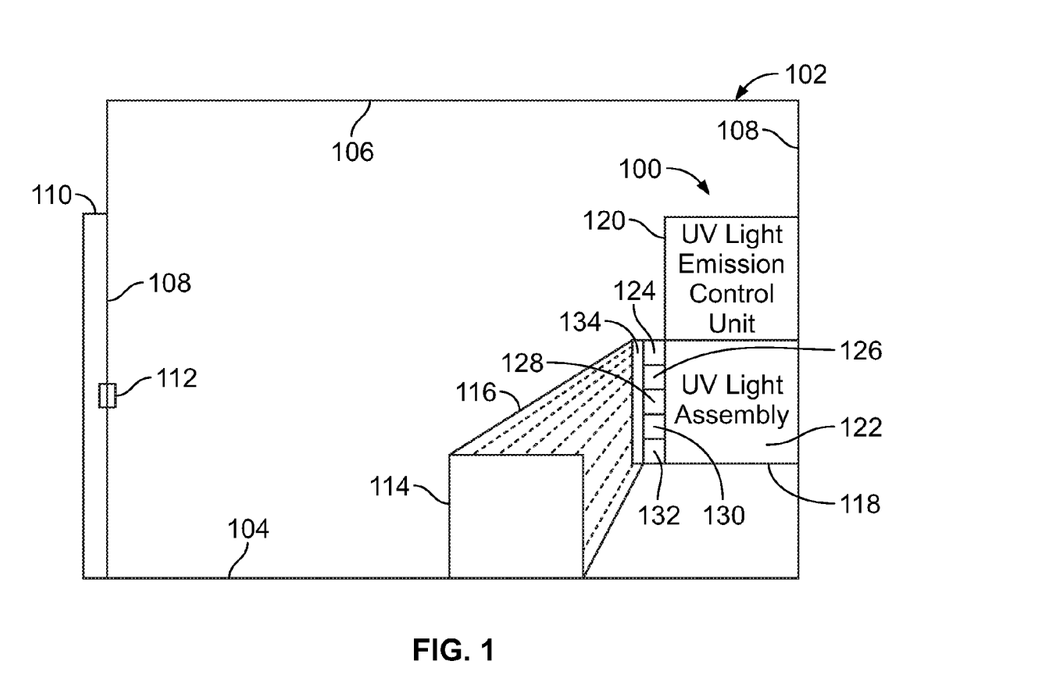
FIG. 1 illustrates a schematic diagram of an ultraviolet light sanitizing system within an enclosed space, according to an embodiment of the present disclosure.

FIG. 1 illustrates a thematic diagram of a UV light sanitizing system 100 within an enclosed space 102, according to an embodiment of the present disclosure. The enclosed space 102 may be defined by a floor 104, a ceiling 106, and walls 108 extending between the floor 104 and the ceiling 106. A door 110 may be moveably secured to one of the walls 108. The door 110 includes a lock 112 that is configured to securely lock the door 110 in a closed position. When the lock 112 is in a locked position, the door 110 is unable to be opened. When the lock 112 is in an unlocked position, the door 110 may be opened. The enclosed space 102 may be a confined space onboard a commercial aircraft. For example, the enclosed space 102 may be a lavatory onboard aircraft. As another example, the enclosed space 102 may be a galley onboard an aircraft. As yet another example, the enclosed space 102 may be a passenger cabin onboard an aircraft. The enclosed space 102 may or may not include the door 110. The enclosed space 102 may be within various other vehicles, structures, and/or the like. For example, the enclosed space 102 may be a room within a commercial, municipal, or residential building, or a room onboard a train, bus, ship, or the like.

The enclosed space 102 includes at least one structure 114 to be sanitized (for example, disinfected, sterilized, or otherwise cleaned) after use. For example, the structure 114 may be a toilet, sink, floor, cabinet, and/or the like within a lavatory of an aircraft.

In order to sanitize the structure 114, the UV light sanitizing system 100 emits multi-wavelength UV light 116 onto and/or into the structure 114. The UV light sanitizing system 100 includes a UV light assembly 118 coupled to a UV light emission control unit 120. The UV light emission control unit 120 is operatively coupled to the UV light assembly 122 through one or more wired or wireless connections. In at least one embodiment, the UV light emission control unit 120 is housed within the UV light assembly 118. In at least one other embodiment, the UV light emission control unit 120 is remotely located from the UV light assembly 118. For example, the UV light assembly 122 is within the enclosed space 102, but the UV light emission control unit 120 may be outside of the enclosed space 102.

The UV light assembly 118 includes a housing 122 that includes a plurality of UV light elements 124, 126, 128, 130, and 132. The housing 122 may include more or less UV light elements than shown. Each UV light element 124, 126, 128, 130, and 132 may be or otherwise include laser(s), lamp(s), light emitting diode(s) (LEDs), microfilament(s), fiber optic element(s), and/or the like. In at least one embodiment, at least two of the UV light elements 124-132 are configured to emit UV light with different UV bands (for example, at different wavelengths and different frequencies). For example, the UV light element 124 may be configured to emit far UV light, while the UV light element 126 may be configured to emit UVC light. The UV light element 128 may be configured to emit UVB light, while the UV light element 130 may be configured to emit UVA light. The UV light element 132 may be configured to emit vacuum UV light. In other embodiments, groups of the UV light elements 124-132 may be configured to emit certain types of UV light. For example, the UV light elements 124 and 126 may be configured to emit far UV light, while the UV light elements 128 and 130 may be configured to emit UVC light.

In at least one embodiment, the UV light elements 124-132 are controlled by the UV light emission control unit 120 to emit variable UV light. For example, in at least one embodiment, the UV light emission control unit 120 is configured to vary the frequency and wavelength of UV light emitted from the UV light elements 124-132 during a sanitizing cycle. For example, for a first portion of the sanitizing cycle, the UV light emission control unit 120 may control the UV light elements 124-132 to emit far UV light, while during a second portion of the sanitizing cycle, the UV light emission control unit 120 may control the UV light elements 124-132 to emit UVC light (such as by modulating the frequency and wavelength of the emitted UV light as compared to the first portion of the sanitizing cycle). The first portion of the sanitizing cycle may be shorter, longer, or the same or similar length of time as the second portion of the sanitizing cycle. For example, during a first portion lasting five seconds or less, the UV light elements 124-132 may emit far UV light onto the structure 114, while during a second portion lasting one minute or less, the UV light elements 124-132 may emit UVC light onto the structure 114.

The UV light emission control unit 120 is configured to control the types of UV light emitted from the UV light elements 124-132 and the amount of time the UV light is emitted based on the type of microbes to be killed during a sanitizing cycle. For example, a first microbe may be resistant to UVC light, but vulnerable to far UV light, while a second microbe may be resistant to far UV light, but vulnerable to UVC light. The UV light emission control unit 120 may be programmed to emit both far UV light and UVC light onto the structure 114, each for a predetermined time, in order to kill both types of microbes.

As shown, the UV light sanitizing system 100 may also include a filter 134 disposed over UV light elements 124-132. The filter 134 may include a plurality of filter segments that are configured to filter UV light emitted from the UV light elements 124-132 with respect to desired UV light bands. In this manner, each of the UV light elements 124-132 may be configured to emit the same type of UV light, but the filter 134 filters the UV light emitted from the UV light elements 124-132 with respect to at least two separate and distinct UV light bands, such as far UV light and UVC light. Alternatively, the UV light sanitizing system 100 may not include the filter 134 (such as if at least two of the UV light elements 124-132 are configured to emit UV light at different UV bands, and/or the UV light emission control unit 120 is configured to emit variable UV light from the UV light elements 124-132).

In operation, the UV light sanitizing system 100 emits UV light onto the structure 114 during a sanitizing cycle, such as when the door 110 is locked, and no one is present within the enclosed space. The UV light emission control unit 120 operates the UV light assembly 122 according to the sanitizing cycle. For example, the UV light emission control unit 120 includes or is otherwise operatively coupled to a memory that stores sanitizing cycle data, which is used by the UV light emission control unit 120 to control the UV light assembly 122. The sanitizing cycle lasts for a predetermined period of time.

During the sanitizing cycle, the UV light assembly 122 emits UV light at different frequency and wavelength bands onto or into the structure 114 in order to kill various microbes that may be present on or in the structure 114. For example, during a first portion of the sanitizing cycle that lasts a first time period, one or more of the UV light elements 124-132 emits UV light within first distinct narrow band (such as far UV light) onto the structure 114. During a second portion of the sanitizing cycle that lasts a second time period (the magnitude of which may be shorter, longer, or equal to the first time period), one or more of the UV light elements 124-132 emits UV light within a second distinct narrow band (such as UVC light) onto or into the structure 114. Multiple distinct UV bands are used to effectively kill a wider variety of microbes, some of which may be resistant to certain types of UV light, but vulnerable to other types of UV light. During a third portion of the sanitizing cycle that lasts a third time period (the magnitude of which may be shorter, longer, or equal to the first and/or second time periods), one or more the UV light elements 124-132 emits UV light within a third distinct narrow band (such as UVB light) onto or into the structure 114. During a fourth portion of the sanitizing cycle that lasts a fourth time period (the magnitude of which may be shorter, longer, or equal to the first, second, and/or third time periods), one or more of the UV light elements 124-132 emits UV light at a fourth distinct narrow band (such as UVA light) onto or into the structure 114. During a fifth portion of the sanitizing cycle that lasts a fifth time period (the magnitude of which may be shorter, longer, or equal to the first, second, third, and/or fourth time periods), one or more of the UV light elements 124-132 emits UV light at a fifth distinct narrow band (such as vacuum UV light) onto or into the structure 114.

The first, second, third, fourth, and fifth time periods may be sequential. That is, the second time period may sequentially follow the first time period, and so on. In at least one other embodiment, at least portions of the time periods may overlap. In at least one other embodiment, the first, second, third, fourth, and fifth time periods may be substantially concurrent.

The sanitizing cycle may include more or less time periods than noted. For example, the sanitizing cycle may include only the first and second time periods noted above. Further, the UV light elements 124-132 may be configured to emit UV light at more or less distinct narrow bands than noted above. For example, during the sanitizing cycle, the UV light elements 124-132 may emit only far UV light and UVC light.

In at least one other embodiment, the UV light emission control unit 120 is configured to operate the UV light elements 124-132 to emit UV light at different narrow bands at the same time, or overlapping in time. For example, at least two of the UV light elements 124-132 may be configured to emit UV light at different narrow bands (for example, far UV light and UVC light) concurrently, simultaneously, or at least partially overlapping in time.

Figure 2:
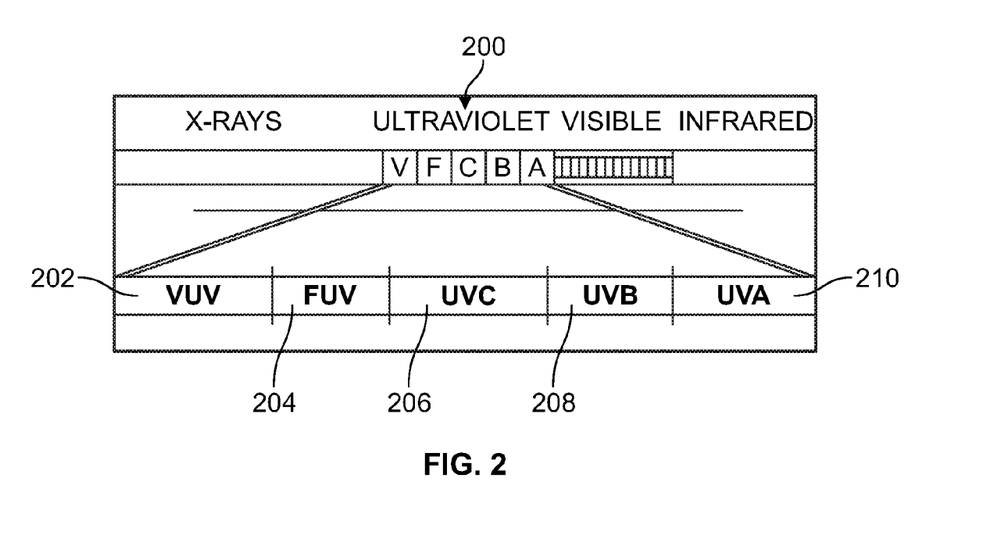
FIG. 2 illustrates an ultraviolet light spectrum.

FIG. 2 illustrates a UV light spectrum 200. As shown, the UV light spectrum 200 includes a plurality of bands, each of which includes a distinct UV range of wavelengths and frequencies. For example, the UV light spectrum 200 includes a vacuum UV narrow band 202, a far UV narrow band 204, a UVC narrow band 206, a UVB narrow band 208, and a UVA narrow band 210. As shown, the bands 202, 204, 206, 208, and 210 are non-overlapping. For example, the vacuum UV narrow band 202 may be below 122 nanometers (nm). The far UV narrow band may be between 122-200 nm. The UVC narrow band 206 may be 200-280 nm. The UVB narrow band 208 may be between 280-315 nm. The UVA narrow band 210 may be between 315-400 nm. Referring to FIGS. 1 and 2, the UV light sanitizing system 100 is configured to emit UV light within at least two of the narrow bands 202, 204, 206, 208, and 210 onto the structure 114.

Notably, frequency and wavelength of light are inversely related. Thus, the higher the frequency, the shorter the wavelength. As such, the frequency of the vacuum narrow band 202 is greater than the frequency of the far UV narrow band 204. In at least one embodiment, the UV light emission control unit 120 is configured to vary the frequency (and therefore the wavelength) of the UV light emitted from one or more of the UV light elements 124-132 to selectively vary the type of UV light emitted from the UV light assembly 122.

Referring to FIGS. 1 and 2, the UV light sanitizing system 100 is configured to sanitize the structure 114 with different types of UV light. The UV light assembly 118 configured to emit the UV light onto the structure 114. The UV light emission control unit 120 is coupled to the UV light assembly 118 (such as through one or more wired or wireless connections), and is configured to control the UV light assembly 118 to separately emit the UV light onto the structure 114 within a first UV band and a second UV band that differs from the first UV narrow band. The first UV band may include one of the far UV light range 202, the UVC light range 206, the UVB light range 208, the UVA light range 210, or the vacuum UV light range 202 within the UV spectrum 200. The second UV band includes another of the far UV light range 204, the UVC light range 206, the UVB light range 208, the UVA light range 210, or the vacuum UV light range 202.

As noted, the UV light within the first band is separately emitted from the UV light within the second band. That is, the emission of UV light within the first band is separate and distinct from the emission of UV light within the second band. The UV light within the first and second bands is not part of an emission of a broad spectrum, range, or portion of the UV light spectrum that includes multiple bands of the UV light. Each band of UV light does not overlap another band of UV light.

Figure 3:
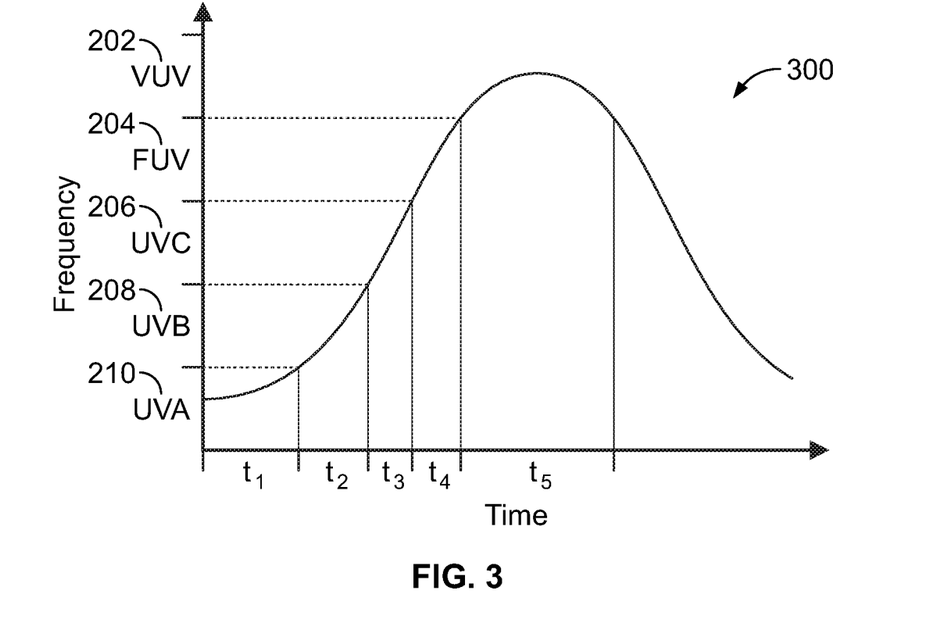
FIG. 3 illustrates a graph of a UV light emission waveform during a sanitizing cycle, according to an embodiment of the present disclosure.

FIG. 3 illustrates a graph of a UV light emission waveform 300 during a sanitizing cycle, according to an embodiment of the present disclosure. It is to be understood that the graph shown in FIG. 3 is a simplified graph and is not drawn to scale. Referring to FIGS. 1-3, the UV light emission control unit 120 may be configured to vary the UV light emitted from the UV light assembly 118 during the sanitizing cycle. For example, during a time period $t_1$, the UV light emission control unit 120 may operate the UV light assembly 118 to emit light at frequencies within the UVA narrow band 210. During a time period $t_2$, the UV light emission control unit 120 may operate the UV light assembly 118 to emit light at frequencies within the UVB narrow band 208. During a time period $t_3$, the UV light emission control unit 120 may operate the UV light assembly 118 to emit light at frequencies within the UVC narrow band 206. During a time period $t_4$, the UV light emission control unit 120 may operate the UV light assembly 118 to emit light at frequencies within the far UV narrow band 204. During a time period $t_5$, the UV light emission control unit 120 may operate the UV light assembly 118 to emit light at frequencies within the vacuum UV narrow band 202.

As shown, the UV light emission control unit 120 may gradually transition the emitted frequencies, such that the UV light emission waveform 300 is shaped like a sine wave. In at least one other embodiment, the UV light emission control unit 120 may maintain and hold a particular frequency for a particular time period and then abruptly change to a different frequency, such that the UV light emission waveform 300 resembles a step waveform.

As shown, the magnitudes of the time periods $t_1$-$t_5$ may not be equal. The UV light emission control unit 120 may be programmed to cause the UV light assembly 118 to emit UV light at different narrow bands at different lengths of time depending on the nature of microbes that are to be eradicated by a particular narrow band of UV light. For example, the UV light within the far UV band 204 may kill a target microbe within only three or four seconds. Alternatively, the time periods $t_1$-$t_5$ may be of equal magnitude.

The UV light emission control unit 120 may vary the UV light with respect to more or less light bands than shown. For example, the UV light emission control unit 120 may vary the emitted light between the far UV band 204 and the UVC band 206.

Figure 4:
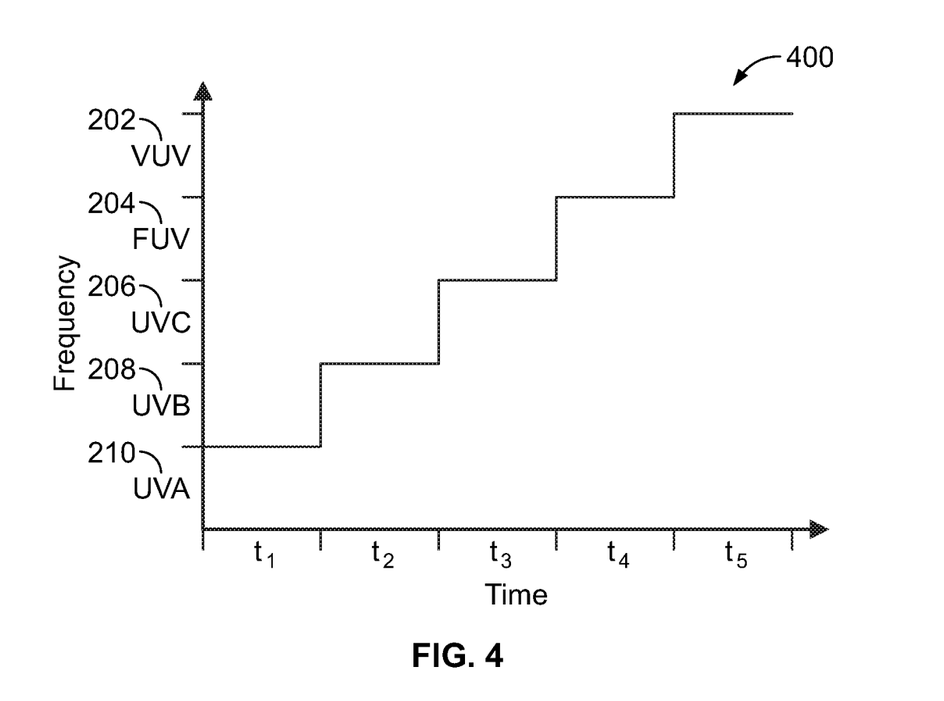
FIG. 4 illustrates a graph of a UV light emission waveform during a sanitizing cycle, according to an embodiment of the present disclosure.

FIG. 4 illustrates a graph of a UV light emission waveform 400 during a sanitizing cycle, according to an embodiment of the present disclosure. It is to be understood that the graph shown in FIG. 4 is a simplified graph and is not drawn to scale. Referring to FIGS. 1-2 and 4, the UV light emission control unit 120 may be configured to vary the UV light emitted from the UV light assembly 118 during the sanitizing cycle, such as shown in FIG. 4. In particular, the UV light emission control unit 120 may maintain a particular frequency within a particular band for a predetermined time period and then abruptly transition to a different particular frequency within a different band for a subsequent time period.

Each of the time periods $t_1$-$t_5$ may be of the same or different magnitude, and may be greater or less than shown. Further, the UV light emission control unit 120 may vary the UV light with respect to more or less light bands than shown. For example, the UV light emission control unit 120 may vary the emitted light between the far UV band 204 and the UVC band 206.

Figure 5:
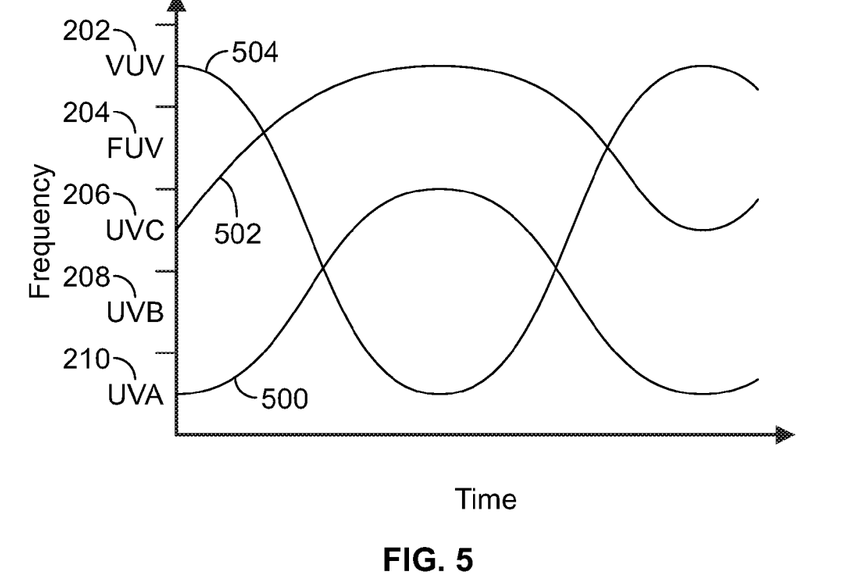
FIG. 5 illustrates a graph of UV light emission waveforms during a sanitizing cycle, according to an embodiment of the present disclosure.

FIG. 5 illustrates a graph of UV light emission waveforms 500, 502, and 504 during a sanitizing cycle, according to an embodiment of the present disclosure. It is to be understood that the graph shown in FIG. 5 is a simplified graph and is not drawn to scale. Referring to FIGS. 1-2 and 5, the UV light emission control unit 120 may be configured to vary the UV light emitted from the UV light assembly 118 during the sanitizing cycle, such as shown in FIG. 5. In particular, at least three different UV light elements 124-132 may emit UV light at different bands at a particular time during the sanitizing cycle. That is, the UV light emission control unit 120 may control multiple different UV light elements 124-132 to emit different UV light during the sanitizing cycle.

As noted, each UV light element 124-132 may emit UV light at a different frequency concurrently, simultaneously, or at least partially overlapping in time during the sanitizing cycle. In at least one other embodiment, a first group of UV light elements 124-132 may emit UV light at a first frequency, while a second group of UV light elements 124-132 may emit UV light at a second frequency that differs from the first frequency. As shown, UV light emission control unit 120 may modulate the frequencies of UV light emitted by the UV light elements 124-132 over time. The UV light emission control unit 120 may control the UV light elements 124-132 of the UV light assembly 118 to concurrently emit more or less different UV light waveforms than shown in FIG. 5.

Referring to FIGS. 1-5, the UV light sanitizing system may be programmed to emit UV light at varying UV bands. The UV light emission control unit 120 controls the UV light assembly 118 to selectively emit narrow bands of UV light across the UV spectrum. For example, the UV light emission control unit 120 controls the UV light assembly 118 to emit two or more of far UV light, UVC light, UVB light, UVA light, and/or vacuum UV light. The types of UV light emitted from the UV light assembly 118 may be selected based on the types of microbes (for example, bacteria, germs, fungi, viruses, spores, and the like) that may be present on the structure 114. As such, the UV light sanitizing system 100 may be specifically tailored to kill particular types of microbes with different types of UV light. The UV light sanitizing system emits multiple high energy, narrow bands of different types of UV light (in contrast to a single broad band of UV light), thereby effectively and efficiently sanitizing the structure 114.

In at least one embodiment, the UV light control unit 120 varies the duration, frequency, order, and/or the like of emitted UV light from the UV light assembly 118 to efficiently sanitize the structure 114, while consuming less power than a typical broad spectrum system. In at least one embodiment, the UV light assembly includes a wide irradiance source and one or more filters 134 that filter the emitted light with respect to desired UV wavelengths and frequencies.

The structure 114 is exposed to UV light within different light bands. The exposure may last ten seconds or less for each narrow band set of UV light, which reduces power consumption. In at least one embodiment, each of the narrow band sets of UV light includes at least one non-overlapping bandwidth of UV light. In at least one embodiment, the total exposure during a sanitizing cycle may be one minute or less. Each narrow band set (such as the bands 202-210) may be particularly suited to kill one or more particular microbes.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the UV light emission control unit 120 may be or include one or more processors that are configured to control operation of UV light assembly 122, as described above.

The UV light emission control unit 120 is configured to execute a set of instructions that are stored in one or more data storage units or elements (such as one or more memories), in order to process data. For example, the UV light emission control unit 120 may include or be coupled to one or more memories. The data storage units may also store data or other information as desired or needed. The data storage units may be in the form of an information source or a physical memory element within a processing machine.

The set of instructions may include various commands that instruct the UV light emission control unit 120 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the UV light emission control unit 120. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the UV light emission control unit 120 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 6:
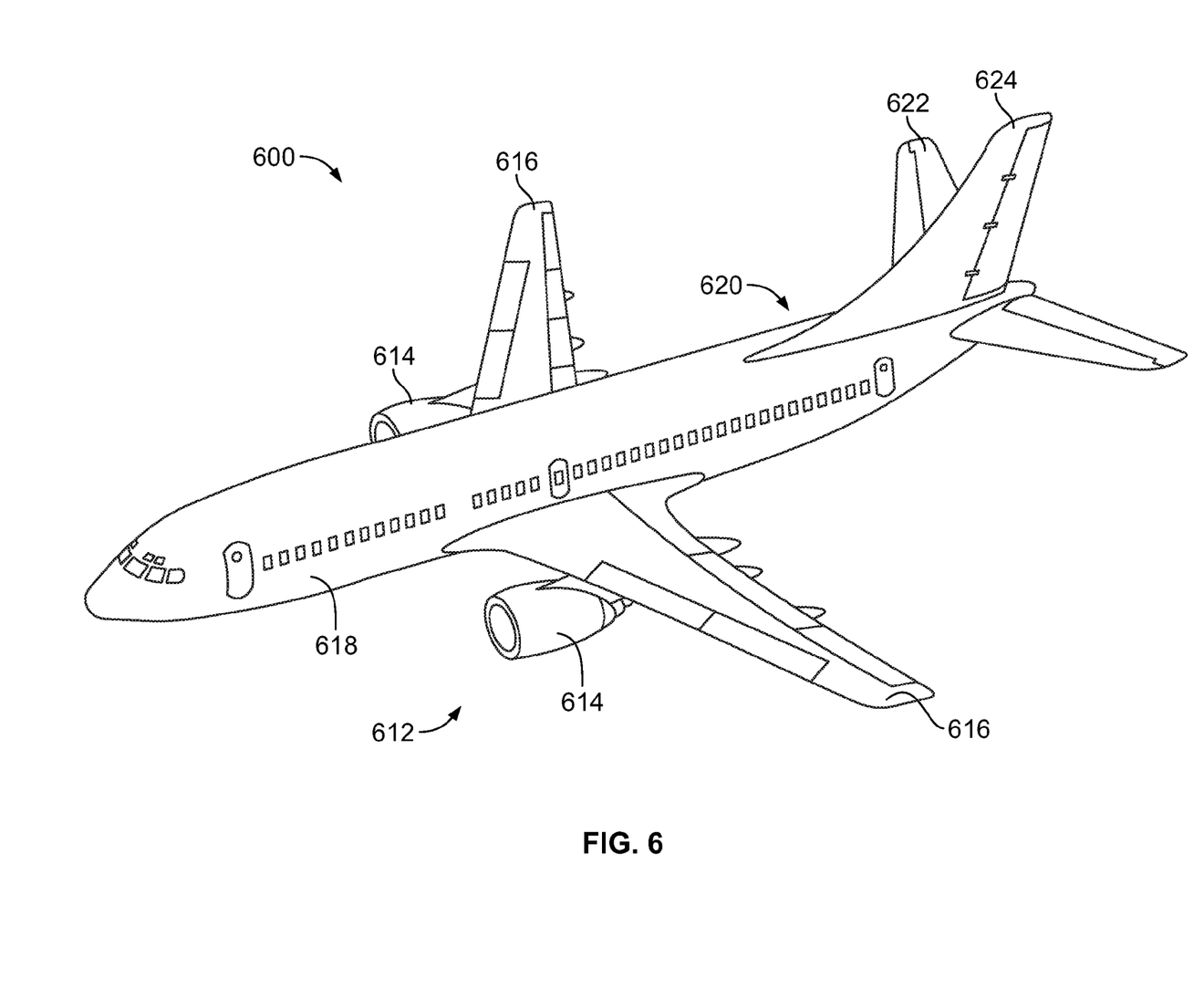
FIG. 6 illustrates a perspective top view of an aircraft, according to an embodiment of the present disclosure.

FIG. 6 illustrates a perspective top view of an aircraft 600, according to an embodiment of the present disclosure. The aircraft 600 includes a propulsion system 612 that may include two turbofan engines 614, for example. Optionally, the propulsion system 612 may include more engines 614 than shown. The engines 614 are carried by wings 616 of the aircraft 600. In other embodiments, the engines 614 may be carried by a fuselage 618 and/or an empennage 620. The empennage 620 may also support horizontal stabilizers 622 and a vertical stabilizer 624.

The fuselage 618 of the aircraft 600 defines an internal cabin, which may include a cockpit, one or more work sections (for example, galleys, personnel carry-on baggage areas, and the like), one or more passenger sections (for example, first class, business class, and coach sections), and an aft section in which an aft rest area assembly may be positioned. Each of the sections may be separated by a cabin transition area, which may include one or more class divider assemblies. Overhead stowage bin assemblies may be positioned throughout the internal cabin. The internal cabin includes one or more chambers, such as lavatories, for example. One or more UV light sanitizing systems 100 (shown and described with respect to FIG. 1) may be located within the internal cabin.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 7A:
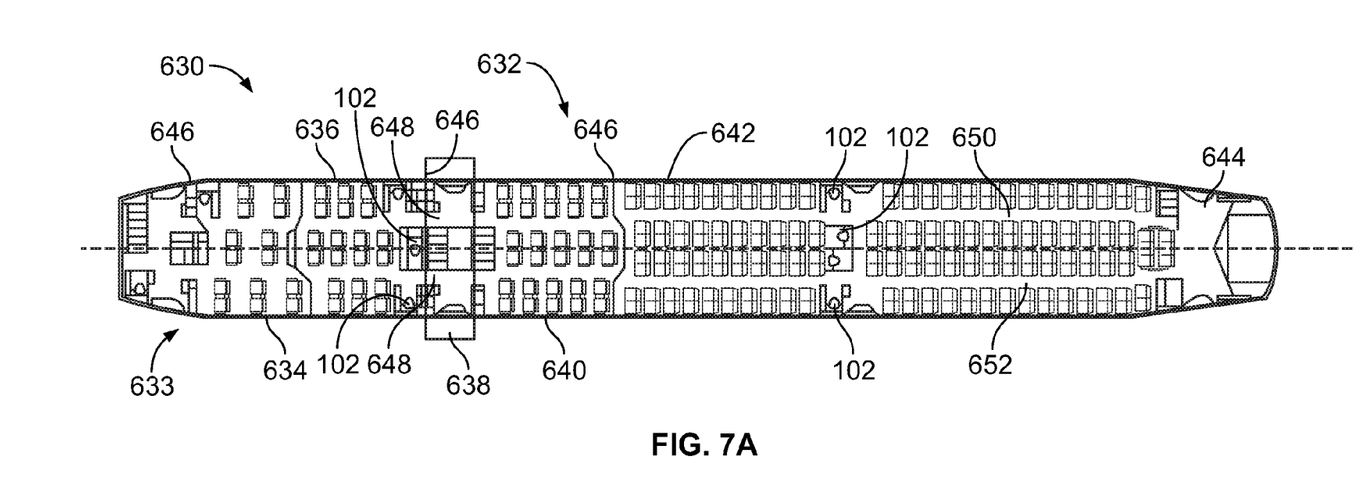
FIG. 7A illustrates a top plan view of an internal cabin of an aircraft, according to an embodiment of the present disclosure.

FIG. 7A illustrates a top plan view of an internal cabin 630 of an aircraft, according to an embodiment of the present disclosure. The internal cabin 630 may be within a fuselage 632 of the aircraft. For example, one or more fuselage walls may define the internal cabin 630. The internal cabin 630 includes multiple sections, including a front section 633, a first class section 634 (or first class suites, cabins, for example), a business class section 636, a front galley station 638, an expanded economy or coach section 640, a standard economy or coach section 642, and an aft section 644, which may include multiple enclosed spaces or chambers 102, such as lavatories and galley stations. It is to be understood that the internal cabin 630 may include more or less sections than shown. For example, the internal cabin 630 may not include a first class section, and may include more or less galley stations than shown. Each of the sections may be separated by a cabin transition area 646, which may include class divider assemblies between aisles 648.

As shown in FIG. 7A, the internal cabin 630 includes two aisles 650 and 652 that lead to the aft section 644. Optionally, the internal cabin 630 may have less or more aisles than shown. For example, the internal cabin 630 may include a single aisle that extends through the center of the internal cabin 630 that leads to the aft section 644.

One or more enclosed spaces 102, such as lavatories, may be located within the internal cabin 630. UV light sanitizing systems 100 may be used to sanitize structures within the lavatories 102, such as described above with respect to FIG. 1.

Figure 7B:
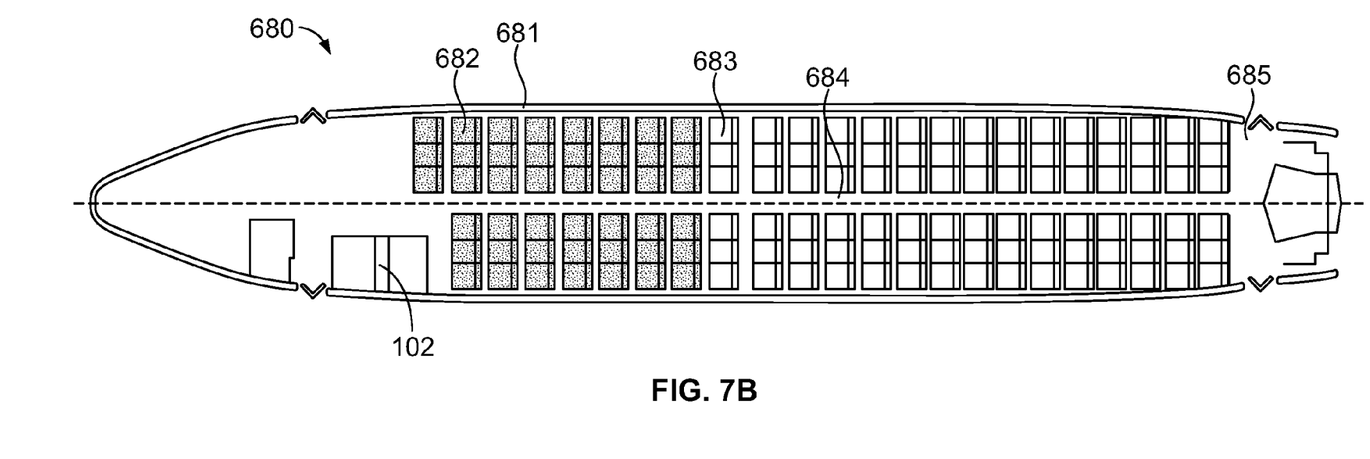
FIG. 7B illustrates a top plan view of an internal cabin of an aircraft, according to an embodiment of the present disclosure.

FIG. 7B illustrates a top plan view of an internal cabin 680 of an aircraft, according to an embodiment of the present disclosure. The internal cabin 680 may be within a fuselage 681 of the aircraft. For example, one or more fuselage walls may define the internal cabin 680. The internal cabin 680 includes multiple sections, including a main cabin 682 having passenger seats 683, and an aft section 685 behind the main cabin 682. It is to be understood that the internal cabin 680 may include more or less sections than shown.

The internal cabin 680 may include a single aisle 684 that leads to the aft section 685. The single aisle 684 may extend through the center of the internal cabin 680 that leads to the aft section 685. For example, the single aisle 684 may be coaxially aligned with a central longitudinal plane of the internal cabin 680.

One or more enclosed spaces 102, such as lavatories, may be located within the internal cabin 680. UV light sanitizing systems 100 may be used to sanitize structures within the lavatories 102, such as described above with respect to FIG. 1.

Figure 8:
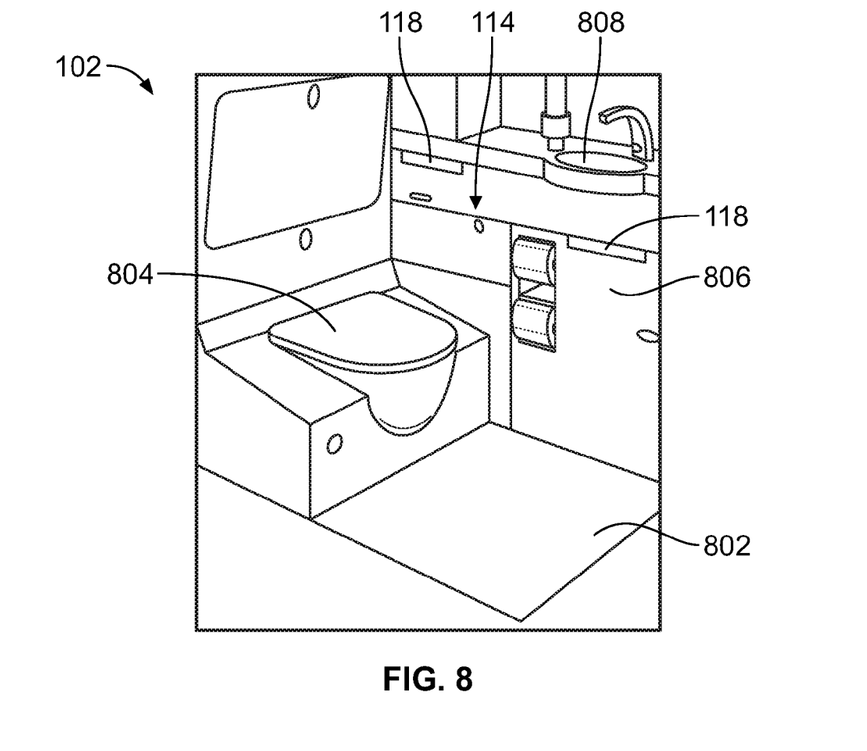
FIG. 8 illustrates a perspective internal view of a lavatory, according to an embodiment of the present disclosure.

FIG. 8 illustrates a perspective internal view of a lavatory 102, according to an embodiment of the present disclosure. As noted, the lavatory 102 is an example of the enclosed space 102 shown and described with respect to FIG. 1. The lavatory 102 may be onboard an aircraft, as described above. Optionally, the lavatory 102 may be onboard various other vehicles. In other embodiments, the lavatory 102 may be within a fixed structure, such as a commercial or residential building.

The lavatory 102 includes a base floor 802 that supports a toilet 804, cabinets 806, and a sink 808. UV light assemblies 118 are secured within the lavatory 102 and are configured to be activated during a sanitizing cycle to sanitize (for example, disinfect, sterilize, or otherwise clean) various structures within the lavatory 102, such as the toilet 804, the floor 802, the cabinets 806, and/or the sink 808.

Figure 9:
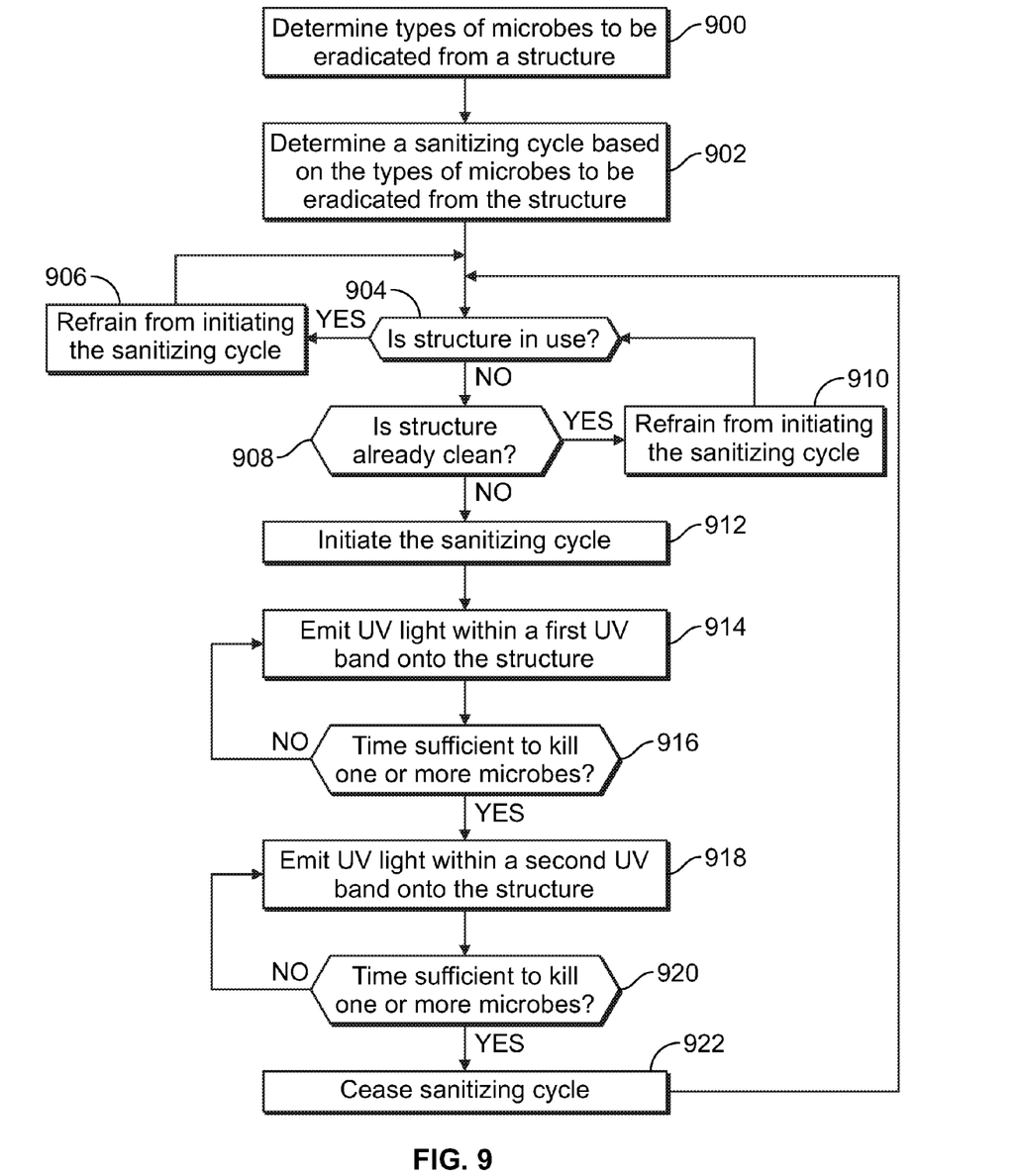
FIG. 9 illustrates a flow chart of a method of sanitizing a structure, according to an embodiment of the present disclosure.

FIG. 9 illustrates a flow chart of a method of sanitizing a structure, according to an embodiment of the present disclosure. Referring to FIGS. 1 and 9, the method begins at 900, in which a determination is made as to the types of microbes that are to be eradicated from the structure 114. Such determination allows for a determination as to the types of UV light that are particularly well-suited for killing the targeted microbes. For example, the UV light emission control unit 120 may store or otherwise access data that correlates types of UV light that with microbes that are effectively and efficiently killed by those types of UV light.

At 902, a sanitizing cycle is determined based on the types of microbes to be eradicated from the structure 114. In at least one embodiment, an individual may input (such as through an input device, such as a keyboard, mouse, touchscreen, or the like) the types of microbes to be targeted, and the UV light emission control unit 120 may determine an efficient sanitizing cycle for the targeted microbes.

After the sanitizing cycle has been determined and stored in memory, at 904, the UV light emission control unit 120 determines whether the structure 114 is in use. For example, the UV light emission control unit 120 may determine that a lavatory is in use based on motion or proximity sensors that are in communication with the UV light emission control unit 120, a door lock sequence, and/or the like. If, at 904, the UV light emission control unit 120 determines that the structure 114 is in use, the UV light emission control unit 120 refrains from initiating the sanitizing cycle at 906.

If, however, the structure is not in use at 904, the UV light emission control unit 120 determines if the structure 114 is already clean at 908. For example, if the structure 114 has not been used subsequent to a previous sanitizing cycle, the UV light emission control unit 120 may determine that the structure 114 is already clean. If the structure 114 is already clean, the method proceeds from 908 to 910, in which the UV light emission control unit 120 refrains from initiating the sanitizing cycle, and the method returns to 904.

If, however, the structure is not clean at 908, the method proceeds from 908 to 912, in which the UV light emission control unit 120 initiates the sanitizing cycle. During the sanitizing cycle, at 914, the UV light emission control unit 120 operates the UV light assembly 118 to emit UV light within a first UV band onto the structure 114. A predetermination may have been made that UV light within the first UV band is particularly suited to kill one or more types of microbes.

At 916, the UV light emission control unit 120 determines whether the time period during which the UV light within the first UV band is emitted is sufficient to kill the type(s) of microbes. If not, the method returns to 914, at which the UV light within the first UV band continues to be emitted onto the structure 114.

If, however, the time is sufficient to kill the microbes at 916 (based on the predetermined sanitizing cycle, for example), the method proceeds from 916 to 918, at which the UV light emission control unit 120 operates the UV light assembly 118 to emit UV light within a second UV band (that is separate and distinct from the first UV band) onto the structure 114. A predetermination may have been made that UV light within the second UV band is particularly suited to kill one or more types of microbes.

At 920, the UV light emission control unit 120 determines whether the time period during which the UV light within the second UV band is emitted is sufficient to kill the type(s) of microbes. If not, the method returns to 918, at which the UV light within the second UV band continues to be emitted onto the structure 114.

If, however, the time is sufficient to kill the microbes at 920 (based on the predetermined sanitizing cycle, for example), the method proceeds from 920 to 922, at which the UV light emission control unit 120 ceases the sanitizing cycle. The method then returns to 904 from 922.

Steps 914 and 920 may occur at different times. Optionally, steps 914 and 920 may be concurrent, or at least partially overlap in time. Additionally, the method may include emission of UV light within third, fourth, fifth, and/or more UV bands.

Referring to FIGS. 1-9, as described above, embodiments of the present disclosure provide systems and methods of efficiently sanitizing a structure using UV light. In particular, embodiments of the present disclosure provide systems and methods of eradicating a wide variety of microbes from a structure through emission of ultraviolet light within multiple UV bands.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An ultraviolet (UV) light sanitizing system configured to sanitize a structure, the UV light sanitizing system comprising:
   a UV light assembly that is configured to emit UV light onto the structure; and
   a UV light emission control unit coupled to the UV light assembly, wherein the UV light emission control unit is configured to control the UV light assembly to separately emit UV light onto the structure within at least a first UV band and a second UV band that differs from the first UV band during a sanitizing cycle that sanitizes the structure, and wherein the UV light within the first and second UV bands is configured to kill at least one type of microbe.

2. The UV light sanitizing system of claim 1, wherein the first UV band comprises one of a far UV light range, a UVC light range, a UVB light range, a UVA light range, or a vacuum UV light range within the UV spectrum, and wherein the second UV band comprises another of the far UV light range, the UVC light range, the UVB light range, the UVA light range, or the vacuum UV light range.

3. The UV light sanitizing system of claim 1, wherein the UV light emission control unit controls the UV light assembly to emit the UV light within the first UV band at a first time period and to emit the UV light within the second UV band at a second time period.

4. The UV light sanitizing system of claim 3, wherein the first time period differs from the second time period.

5. The UV light sanitizing system of claim 3, wherein the second period of time sequentially follows the first period of time.

6. The UV light sanitizing system of claim 3, wherein the first time period is concurrent with the second time period.

7. The UV light sanitizing system of claim 3, wherein the first time period at least partially overlaps the second time period.

8. The UV light sanitizing system of claim 1, wherein the UV light assembly comprises a plurality of UV light elements.

9. The UV light sanitizing system of claim 8, wherein a first one of the plurality of UV light elements is configured to emit the UV light within the first UV band, and wherein a second one of the plurality of UV light elements is configured to emit the UV light within the second UV band.

10. The UV light sanitizing system of claim 8, wherein the UV emission control unit is configured to modulate the UV light emitted by the plurality of UV light elements to selectively emit the UV light within the first and second UV bands.

11. The UV light sanitizing system of claim 8, wherein the UV light assembly further comprises at least one filter coupled to the plurality of UV light elements, wherein the filter is configured to filter the UV light with respect to the first and second UV bands.

12. An ultraviolet (UV) light sanitizing method configured to sanitize a structure, the UV light sanitizing method comprising:
    coupling a UV light emission control to a UV light assembly; and
    emitting UV light from the UV light assembly onto the structure, wherein the emitting comprises using the UV light emission control unit to control the UV light assembly to separately emit the UV light onto the structure within at least a first UV band and a second UV band that differs from the first UV band during a sanitizing cycle that sanitizes the structure, and wherein the UV light within the first and second UV bands is configured to kill at least one type of microbe.

13. The UV light sanitizing method of claim 12, wherein the emitting comprises using the UV light emission control unit to control the UV light assembly to separately emit the UV light onto the structure within at least a first UV band comprising one of a far UV light range, a UVC light range, a UVB light range, a UVA light range, or a vacuum UV light range within the UV spectrum and a second UV band comprising another of the far UV light range, the UVC light range, the UVB light range, the UVA light range, or the vacuum UV light range during the sanitizing cycle that sanitizes the structure.

14. The UV light sanitizing method of claim 12, wherein the emitting comprises:
    controlling, using the UV light emission control unit, the UV light assembly;

emitting, through the controlling, the UV light within the first UV band at a first time period; and emitting, through the controlling, the UV light within the second UV band at a second time period.

15. The UV light sanitizing method of claim 12, wherein the emitting comprises:

emitting the UV light within the first UV band from a first UV light element of the UV light assembly; and emitting the UV light within the second UV band from a second UV light element of the UV light assembly.

16. The UV light sanitizing method of claim 12, wherein the emitting comprises:

modulating the UV light emitted by the UV light assembly; and selectively emitting, by way of the modulating, the UV light within the first and second UV bands.

17. The UV light sanitizing method of claim 12, wherein the emitting comprises filtering, using at least one filter coupled to the plurality of UV light elements, the UV light with respect to the first and second UV bands.

18. A vehicle comprising:

an internal cabin;

a lavatory within the internal cabin; and an ultraviolet (UV) light sanitizing system that is configured to sanitize at least one structure within the lavatory, the UV light sanitizing system comprising:

a UV light assembly that is configured to emit UV light onto the at least one structure, wherein the UV light assembly comprises a plurality of UV light elements; and a UV light emission control unit coupled to the UV light assembly, wherein the UV light emission control unit is configured to control the UV light assembly to separately emit UV light onto the at least one structure within at least a first UV band and a second UV band that differs from the first UV band during a sanitizing cycle that sanitizes the at least one structure, wherein the first UV band comprises one of a far UV light range, a UVC light range, a UVB light range, a UVA light range, or a vacuum UV light range within the UV spectrum, wherein the second UV band comprises another of the far UV light range, the UVC light range, the UVB light range, the UVA light range, or the vacuum UV light range, and wherein the UV light within the first and second UV bands is configured to kill at least one type of microbe.

19. The vehicle of claim 18, wherein the UV light emission control unit controls the UV light assembly to emit the UV light within the first UV band at a first time period and to emit the UV light within the second UV band at a second time period, wherein the first time period is one of concurrent with, different from, sequentially following, or partially overlapping the second time period.

20. The vehicle of claim 18, wherein the UV emission control unit is configured to modulate the UV light emitted by the plurality of UV light elements to selectively emit the UV light within the first and second UV bands.

* * * * *